(12) United States Patent
Klocke

(10) Patent No.: US 9,731,050 B2
(45) Date of Patent: Aug. 15, 2017

(54) ENDOPROSTHESIS

(75) Inventor: Bjoern Klocke, Zurich (CH)

(73) Assignee: BIOTRONIK VI PATENT AG, Baar (CH)

( * ) Notice: Subject to any disclaimer, the term of this patent is extended or adjusted under 35 U.S.C. 154(b) by 1560 days.

(21) Appl. No.: 12/507,367

(22) Filed: Jul. 22, 2009

(65) Prior Publication Data

US 2010/0191324 A1    Jul. 29, 2010

(30) Foreign Application Priority Data

Jul. 23, 2008  (DE) .................... 10 2008 040 640

(51) Int. Cl.
*A61F 2/07* (2013.01)
*A61L 31/02* (2006.01)
*A61L 31/10* (2006.01)
*A61L 31/14* (2006.01)

(52) U.S. Cl.
CPC ............. *A61L 31/022* (2013.01); *A61L 31/10* (2013.01); *A61L 31/148* (2013.01)

(58) Field of Classification Search
CPC ............. A61F 2310/00041; A61F 2/07; A61F 2250/0036; A61F 2310/00221; A61F 2250/0068; A61L 27/32; A61L 31/16; A61L 31/10; A61L 31/082; C04B 41/515; C04B 41/5177
USPC ............ 623/1.1, 1.15, 1.38, 1.46, 1.49–1.54; 427/2.24–2.26
See application file for complete search history.

(56) References Cited

U.S. PATENT DOCUMENTS 3,715,371 A * 2/1973 Thomson .............. C07F 7/1836
                                                    156/326
4,031,062 A * 6/1977 Shirayama ............... C08F 8/42
                                                    156/334
6,027,527 A * 2/2000 Asano et al. ................ 623/1.15
(Continued)

FOREIGN PATENT DOCUMENTS

DE        20 2005 006        10/2005
DE        10 2005 039        2/2007
(Continued)

OTHER PUBLICATIONS foreign translation of WO 05/65576 espace.net, pp. 1-3.*
(Continued)

*Primary Examiner* — Brian Pellegrino
(74) *Attorney, Agent, or Firm* — Greer, Burns & Crain, Ltd.; Steve P. Fallon

(57) ABSTRACT

An endoprosthesis, in particular an intraluminal endoprosthesis, for example a stent, having a basic mesh composed of an at least predominantly biodegradable material, and a coating provided on the biodegradable material is proposed. For better control of the degradation the basic mesh is essentially completely covered by a coating which contains parylene, preferably at least predominantly parylene, particularly preferably parylene C or parylene N, and the basic mesh is essentially completely covered by the coating, whereby the thickness of the coating is between approximately 0.1 μm and approximately 10 μm, preferably between approximately 0.4 μm and approximately 7 μm, particularly preferably between approximately 1 μm and approximately 5 μm. Also proposed is a method for manufacturing such an endoprosthesis.

19 Claims, 5 Drawing Sheets

(56) References Cited

U.S. PATENT DOCUMENTS

| | | | |
|---|---|---|---|
| 6,174,329 B1* | 1/2001 | Callol et al. | 623/1.46 |
| 2004/0249472 A1* | 12/2004 | Liu et al. | 623/23.53 |
| 2005/0196424 A1 | 9/2005 | Chappa | |
| 2005/0283228 A1* | 12/2005 | Stanford | A61F 2/91 623/1.15 |
| 2006/0064160 A1* | 3/2006 | Gerold et al. | 623/1.38 |
| 2006/0106455 A1* | 5/2006 | Furst et al. | 623/1.31 |
| 2006/0224237 A1 | 10/2006 | Furst et al. | |
| 2006/0241742 A1* | 10/2006 | Harder et al. | 623/1.42 |
| 2006/0276878 A1* | 12/2006 | Owens et al. | 623/1.15 |
| 2007/0021834 A1* | 1/2007 | Young et al. | 623/16.11 |
| 2007/0050009 A1 | 3/2007 | Flanagan | |
| 2008/0071358 A1* | 3/2008 | Weber et al. | 623/1.46 |
| 2011/0011841 A1* | 1/2011 | Hanaki | C09J 7/0271 219/121.72 |
| 2014/0004312 A1* | 1/2014 | Foreman et al. | 427/2.24 |

FOREIGN PATENT DOCUMENTS

| | | | |
|---|---|---|---|
| DE | 10 2007 004 | 7/2008 | |
| DE | 10 2007 034 | 1/2009 | |
| EP | 0 747 069 | 12/1996 | |
| EP | 2 018 882 | 1/2009 | |
| JP | 2007075486 A * | 3/2007 | A61L 27/00 |
| WO | WO 2005/065576 | 7/2005 | |
| WO | WO 2008/034474 A2 | 3/2008 | |
| WO | WO 2008/092436 | 8/2008 | |

OTHER PUBLICATIONS abstract of JP document75486.*
German Patent Office, Search Report for Priority German Application No. 10 2008 040 640.6 Issued Jul. 24, 2009.
European Patent Office, Search Report for corresponding EP Patent Application No. 09163889.0/1219/2147688 Issued Jan. 16, 2013.

* cited by examiner

ENDOPROSTHESIS

FIELD OF THE INVENTION

The invention relates to an endoprosthesis or implant, in particular an intraluminal endoprosthesis, for example a stent.

BACKGROUND OF THE INVENTION

Stents are endovascular prostheses which may be used for the treatment of stenoses (vasoconstriction). Stents have a tubular or hollow cylindrical basic mesh which is open at both longitudinal ends. The tubular basic mesh, composed of the base material of such an endoprosthesis, is inserted into the blood vessel to be treated and is used to support the vessel.

Such stents have become established for the treatment of vascular diseases in particular. Use of stents allows constricted regions in blood vessels to be expanded, resulting in lumen gain. Although the optimal vessel cross section primarily necessary for successful treatment may be achieved by the use of stents, the permanent presence of such a foreign body initiates a cascade of microbiological processes which may lead to gradual overgrowth of the stent, and in the worst case may result in vascular occlusion. A starting point for solving this problem consists in producing the stent from a biodegradable material.

The term "biodegradation" refers to hydrolytic, enzymatic, and other metabolic chemical degradation processes in the living organism which are primarily caused by the bodily fluids which come into contact with the endoprosthesis, resulting in gradual dissolution of at least large portions of the endoprosthesis. The term "biocorrosion" is often used synonymously for "biodegradation." The term "bioabsorption" includes the subsequent absorption of the degradation products by the living organism.

Suitable materials for the basic mesh of biodegradable endoprostheses may be of a polymeric or metallic nature, for example. The basic mesh may also be composed of several materials. These materials share the common feature of biodegradability. Examples of suitable polymeric compounds include polymers from the group comprising cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyortho esters, polyethylene terephtalate (PET), polymalonic acid (PML), polyanhydrides, polyphosphazenes, polyamino acids, and the copolymers thereof, as well as hyaluronic acid. Depending on the desired characteristics, the polymers may be present in pure form, derivatized form, in the form of blends, or as copolymers. Metallic biodegradable materials are based on alloys of magnesium, iron, zinc, and/or tungsten. The present invention preferably relates to stents or other endoprostheses whose biodegradable material contains magnesium or a magnesium alloy, particularly preferably the alloy WE43, and/or a biodegradable polymer, particularly preferably PLLA. As base materials for stents, these materials have a particularly suitable combination of mechanical, biological, and corrosive properties.

Stents which have coatings for various functions are presently known. Implementation of biodegradable implants involves the problem of controlling the degradability corresponding to the intended therapy. It has not been possible thus far to design a stent which loses its integrity within the target corridor of four weeks to six months, which is important for many therapeutic applications. In this regard "integrity," i.e., mechanical integrity, refers to the characteristic that the stent or endoprosthesis does not undergo hardly any mechanical losses compared to the undegraded stent. This means that the stent is still mechanically stable enough to ensure that the collapse pressure drops only slightly, i.e., to a maximum of 80% of the nominal value. Thus, when integrity is present the stent is still able to meet its primary function of keeping the blood vessel open. Alternatively, integrity may be defined such that the stent is mechanically stable enough that in a load state in the blood vessel it undergoes minimal changes in its geometry, for example does not show appreciable collapse, i.e., under a load of at least 80% of the dilation diameter, or has very little breakage of supporting struts.

Degradable magnesium stents have proven to be particularly promising for the referenced target corridor of degradation, although on the one hand they lose their mechanical integrity or supporting effect too soon, and on the other hand show great fluctuations in loss of integrity both in vitro and in vivo. This means that for magnesium stents the collapse pressure drops too rapidly over time, and/or the drop in the collapse pressure varies too greatly and therefore cannot be determined.

Basically, there are three known approaches for adjusting the desired target time window for the loss of integrity. First, a thicker optimized stent design may be selected. Second, an optimized, slowly degrading magnesium alloy may be used for the stent, or third, surface layers may be provided which delay or accelerate the onset of degradation of the magnesium basic mesh, and/or influence the point in time that degradation begins. The possibility of varying the degradation characteristics according to the first or second approach is greatly limited, and may not be sufficient for an economical and clinically satisfactory solution. With regard to the first approach, in order to ensure ease of insertion of the stent and due to the limited blood vessel dimensions, wall thicknesses of greater than 200 µm are not advisable. For the second approach, only a very limited spectrum of biocompatible and moderately rapidly degradable alloys is known. With regard to the third approach, only fluorine passivation is known.

The above-referenced passivation layers have two fundamental disadvantages which result, among other reasons, from the fact that such stents usually assume two states, namely, a compressed state with a small diameter and an expanded state with a larger diameter. In the compressed state the stent can be inserted into the blood vessel to be supported by using a catheter, and positioned at the site to be treated. The stent is then dilated at the treatment site using a balloon catheter, for example, or, if a shape memory alloy is used as stent material, is converted to the expanded state, for example by heating above the transition temperature. As a result of this change in diameter the basic mesh of the stent is subjected to mechanical stress. Additional mechanical stresses on the stent may occur during manufacturing, or when the stent moves in or with the blood vessel in which the stent is inserted. Thus, the referenced passivation results in the disadvantage that during deformation of the implant microcracks are produced which lead to infiltration of the coating material, thereby reducing the passivation effect of the coating, which causes nonspecific localized degradation. In addition, the onset and speed of degradation depend on the size and distribution of the microcracks, which are defects that are difficult to monitor. This results in a large dispersion in the degradation times.

WO 2005/065576 A1 discloses control of the degradation of degradable implants by use of a coating made of a biodegradable material. Location-dependent degradation of the implant is optimized by the fact that the base body has an in vivo location-dependent first degradation characteristic and a coating which covers the base body completely or only in places and consists of at least one biodegradable material, the coating having an in vivo second degradation characteristic. The cumulative degradation characteristic at a location is obtained from the sum of the respective degradation characteristics of the material and the coating at the given location. The location-dependent cumulative degradation characteristic is specified by varying the second degradation characteristic in such a way that the degradation takes place at the given location during a predetermined time period at a predeterminable degradation rate.

The degradation characteristic of the biodegradable coating described in WO 2005/065576 A1 is achieved in a very general manner, in particular by varying the morphological structure of the coating, by substantive modification of the material, and/or by adjusting the layer thickness of the coating. In this regard "morphological structure" is understood to mean the conformation and aggregation of the compounds which form the coating. The cited document references hyaluronic acid as an example of a coating.

U.S. 2006/0224237 A1 likewise describes a transplant or stent having a protective layer which is used to protect surface structures of the stent from destruction. The surface structures may be formed from one or more materials which are at least partially dissolved, degraded, or absorbed under various environmental conditions.

The possibilities stated in the cited documents for influencing the degradation do not include satisfactory approaches for endoprostheses which degrade within the referenced target corridor. WO 2005/065576 A1 describes only very general principles which do not provide specific approaches in particular for magnesium stents.

U.S. 2007/0050009 A1 concerns a stent having a support structure composed of biodegradable material. This support structure is at least partially provided with an absorption inhibitor layer which reduces the rate of absorption of the support structure. The absorption inhibitor layer itself is likewise absorbed by the surrounding bodily fluids. This known approach as well provides only very limited control of degradation of the stent, which for many applications is inadequate. Hyaluronic acid, collagen, or polyglycolic acid are referenced as examples of materials for an absorption inhibitor layer.

DE 10 2005 039 126 A1 and U.S. 2005/0196424 A1, among other sources, describe coatings with parylene as a protective layer, in particular for prevention of restenosis or inflammation after implantation or as a pretreatment layer for a carrier of bioactive materials. Use of these coatings for the control of degradation is not disclosed.

SUMMARY OF THE INVENTION

The object of the present invention, therefore, is to provide an endoprosthesis whose mechanical supporting effect persists for a fairly long period of time, and whose degradation takes place at a controllable point in time, in particular within the referenced target corridor. In addition, it should be possible to adapt the degradation to the geometric factors of the stent design and the associated clinical requirements.

The object is achieved by use of an endoprosthesis having a coating which contains parylene, preferably at least predominantly parylene, particularly preferably parylene C or parylene N, whereby the basic mesh is essentially completely, preferably completely, covered by the coating, and the thickness of the coating is between approximately 0.1 µm and approximately 10 µm, preferably between approximately 0.4 µm and approximately 7 µm, particularly preferably between approximately 1 µm and approximately 5 µm.

When the layer thickness of the layer containing parylene is greater than 10 µm, due to the considerable thickness the coating results in an appreciable reduction in the lumen through which blood flows in the blood vessel of the patient (also due to the induced neointima formation, among other factors). When the layer thickness is less than 0.1 µm, inhomogeneities related to the layer thickness as well as defects form in the coating. As a result, the degradation of the endoprosthesis basic mesh situated therebelow cannot be reliably prevented, or the degradation proceeds with excessive and undesired variability.

The parylene coating, preferably the coating composed at least of 30% by weight parylene, particularly preferably composed of at least 60% by weight parylene, most particularly preferably composed of at least 90% by weight parylene, in each case preferably composed of parylene C and/or parylene N, has a positive influence on the degradation characteristic. This is achieved in particular by the fact that parylene surprisingly represents a diffusion retardant which, as a function of the layer thickness of the parylene coating, limits the diffusion of water and/or possibly other ions or molecules in the surrounding bodily fluid, such as chloride ions, which for metallic basic meshes have a strong accelerating effect on the degradation as the result of attack of the oxide or passivation layer, to the surface of the basic mesh compared to an uncoated basic mesh. For basic meshes containing magnesium, the hydrogen generated by the degradation of magnesium is able to diffuse outwardly through the coating and from the surface of the basic mesh without appreciable bubble formation as the result of its low level of molecular expansion and nonpolar bonding. In addition, the degradation of the basic mesh is retarded and/or homogenized due to the fact that the cells (in particular macrophages) which play a role in the localized degradation are not able to directly reach the surface of the basic mesh. In this manner the speed of degradation can be controlled in accordance with clinical requirements.

Furthermore, the parylene-containing coating according to the invention advantageously has a flexible design. In this regard the feature of the coating having a flexible design means that the coating follows the movement of the basic mesh, so that essentially no major cracks or the like form in the coating material. This means that the material of the coating itself has no supporting function; i.e., the coating is designed to be elastic and therefore flexible. The elasticity and flexibility of the body and the coating are greater the more intense the degradation of the basic mesh situated beneath the coating, whereby the degradation continues, at a decreased speed, beneath the coating. After complete degradation the flexible coating, which has no supporting function itself, moves flexibly together with the blood vessel being treated—in the wall of which the coating is typically embedded by endotheliazation and sometimes also by neointimal proliferation—and the bodily fluid flowing therein.

The parylene-containing coating according to the invention is therefore flexible, and also has a low swelling volume. In this manner the desired loss of integrity may be adjusted to the desired time, in particular four weeks to six months.

"Parylene" refers to completely linear, partially crystalline, and uncrosslinked aromatic polymers. Depending on their structure, these polymers may be divided into four different basic types: parylene C, parylene D, parylene N, and parylene F.

As a result of the parylene-containing coating, the surface of the endoprosthesis, i.e., of the basic mesh, is protected by the cover layer in such a way that, in contrast to known passivation, the surface withstands mechanical stresses such as crimping, dilation, or crossing of the lesion without the formation of undesired cracks or other defects. In this manner uncontrolled degradation of the endoprosthesis at unwanted locations is prevented. Large dispersion of the degradation times may be prevented by the avoidance of uncontrolled crack or defect formation in a flexible coating.

In the degradation of an endoprosthesis according to the invention, the degraded endoprosthesis material diffuses at least partially through the parylene coating, with a thin tube composed of the coating or possibly decomposition products of the degraded endoprosthesis material being maintained. For an endoprosthesis made of a magnesium alloy, soft magnesium decomposition or conversion products such as calcium phosphate (from the body's own buffer system), and possibly magnesium hydroxide or magnesium phosphate, for example, are produced. The occurrence of such products is clinically acceptable in the selection of suitable biocompatible alloys.

The parylene coating may preferably be applied using a plasma coating process, the material being characterized by a high gap clearance which allows complete coverage of the basic mesh. The thickness of the parylene coating which is preferably applied using the plasma coating process, preferably the coating containing parylene C or parylene N, is between approximately 0.1 µm and approximately 10 µm, preferably between approximately 0.4 µm and approximately 7 µm, particularly preferably between approximately 1 µm and approximately 5 µm. For a layer thickness greater than 10 µm the coating time becomes too long and the coating process is therefore too costly.

In one preferred exemplary embodiment the parylene coating has regions in which the layer thickness is locally reduced compared to the other regions. However, the layer thickness in the regions with reduced layer thickness is still in the thickness range stated above, whereby the regions of reduced layer thickness have a thickness, for example, of greater than 0% to approximately 70%, particularly preferably from approximately 5% to approximately 50%, of the thickness in the other regions.

As a result of the regions with reduced layer thickness, which may be situated at various locations in the basic mesh (see below for examples), it is possible to control the spatial distribution of the start of a somewhat accelerated onset of degradation, since the degradation proceeds more rapidly in the regions with reduced layer thickness. For example, in many cases it is suitable when the longitudinal connectors (connecting webs) of the stent degrade much more quickly than the supporting annular or helical elements. For production of the regions with reduced layer thickness, the coating may be structured using the methods described below. This results in troughs or grooves, for example, having a lateral macroscopic or microscopic extension (typically between 1 µm and 1 mm). The geometric structuring is selected so that the desired (locally controlled) degradation kinetics for the endoprosthesis result.

The parylene coating may also be applied in such thin layers (depending on the material and characteristics of the basic mesh surface, with a thickness of approximately 0.1 µm to 1 µm) that the layer is not completely closed, but instead is still in a phase of island growth, so that between the islands of parylene-containing coating recesses or thinner regions of the layer are formed by the portions of the surface which have little or no coating. Onset of degradation takes place in these regions first after implantation of the endoprosthesis according to the invention.

Alternatively, specific predefined regions of reduced layer thickness may also be produced from the parylene coating by the fact that during dilation of the stent in the lesion the specified regions undergo much greater deformation than other regions due to a specialized design of the stent body, for example a smaller diameter. This causes the parylene layer to be drawn out lengthwise, and thus made thinner, at these locations.

In one exemplary embodiment of the present invention, an additional layer containing a carrier and at least one pharmaceutically active substance may be applied to the parylene-containing coating. The carrier in a manner of speaking absorbs the pharmaceutically active substance.

Within the meaning of the invention, a "pharmaceutically active substance" (or therapeutically active or effective substance, medicament, active ingredient) is understood to mean a plant, animal, or synthetic active substance (medicament) or a hormone which in appropriate dosages is used as a therapeutic agent for influencing states or functions of the body, as a substitute for active substances such as insulin which are naturally produced by the human or animal body, and for eliminating or rendering harmless pathogenic agents, tumors, cancer cells, or substances foreign to the body. The release of the substance into the environment of the endoprosthesis has a positive effect on the healing process, or counteracts pathological changes in the tissue resulting from surgical procedures, or in the field of oncology is used to render malignant cells harmless.

These types of pharmaceutically active substances have an anti-inflammatory and/or antiproliferative and/or spasmolytic effect, for example, by means of which restenosis, inflammation, or (vascular) spasms, for example, may be avoided. In particularly preferred exemplary embodiments, such substances may be composed of one or more substances of the active substance group of calcium channel blockers, lipid regulators (fibrates, for example), immunosuppressants, calcineurin inhibitors (tacrolimus, for example), antiphlogistic agents (cortisone or dichlofenac, for example), anti-inflammatory agents (imidazole, for example), antiallergic agents, oligonucleotides (dODN, for example), estrogens (genistein, for example), endothelium-forming agents (fibrin, for example), steroids, proteins, hormones, insulins, cytostatic agents, peptides, vasodilators (sartane, for example), and substances with antiproliferative activity, analgesics, antirheumatic agents, and cytostatic agents, preferably cyclosporin A, taxole, or taxane, in the present case preferably paclitaxel or limus compounds, preferably sirolimus (rapamycin), zotarolimus, tacrolimus, biolimus, and everolimus.

The thickness of the at least one active substance-bearing layer is approximately 0.1 µm to approximately 40 µm, preferably between approximately 0.6 µm and approximately 15 µm, particularly preferably between approximately 1 µm and approximately 10 µm. The layer may be composed of multiple individual layers. The loading with medicament is approximately 1% by weight to 90% by weight, preferably between approximately 5% by weight and approximately 80% by weight, particularly preferably between approximately 10% by weight and approximately 60% by weight.

The advantage of this exemplary embodiment is that as the result of the parylene-containing coating the medicament-loaded layer is effectively isolated from the degradation of the stent, thus allowing the medicament to be effectively eluted in the blood vessel. To further improve the activity of the stent by limiting proliferation and/or inflammation, a suitable medicament (paclitaxel or sirolimus and the derivatives thereof) may be applied to the stent, and is then eluted in vivo over a suitable time period. This may be achieved by introduction into surface cavities or a carrier substance (typically a polymer). Use of such medicaments on degradable stents results in the additional advantage that the chemical action of decomposition products of the base body (for example, $OH^-$ions for Mg or $H^+$ions for PLLA) on the medicament and the elution of medicament is suitably reduced in such a way that a sufficient, effective quantity of the medicament is eluted, and the medicament is not destroyed, or its activity is not appreciably impaired, as a result of the degradation-related pH shift or other chemical processes occurring during degradation.

Examples of advantageous polymer carriers include poly-D,L-lactide, PEVA-PBMA (Cypher), SIBS (Taxus), polyethersulfone or polyesters. Fats may also be used as the carrier (substrate, matrix). Further polymers present in the active substance-containing layer are preferably selected from the group comprising the following:

Nondegradable polymers, for example polyethylene; polyvinyl chloride; polyacrylates, preferably polyethyl and polymethyl acrylates, polymethyl methacrylate, polymethyl-co-ethyl acrylate, and ethylene/ethyl acrylate; polytetrafluoroethylene, preferably ethylene/chlorotrifluoroethylene copolymers, ethylene/tetrafluoroethylene copolymers; polyamides, preferably polyamideimide, PA-11, PA-12, PA-46, PA-66; polyetherimide; polyethersulfone; poly(iso)butylene; polyvinyl chloride; polyvinyl fluoride; polyvinyl alcohol; polyurethane; polybutylene terephthalate; silicones; polyphosphazene; polymer foams, preferably polymer foams composed of carbonates or styrenes; copolymers and/or blends of the listed polymer classes, and polymers of the class of thermoplasts;

Degradable polymers, for example polydioxanone; polyglycolide; polycaprolactone; polylactides, preferably poly-L-lactide, and copolymers and blends thereof, preferably poly(L-lactide-co-glycolide), poly(D,L-lactide-co-glycolide), poly(L-lactide-co-D,L-lactide), poly (L-lactide-co-trimethylene carbonate); triblock copolymers; polysaccharides, preferably chitosan, levan, hyaluronic acid, heparin, dextran, cellulose; polyhydroxy valerate; ethyl vinyl acetate; polyethylene oxide; polyphosphorylcholine; fibrin; albumin; polyhydroxybutyric acid, preferably atactic, isotactic, and/or syndiotactic polyhydroxybutyric acid, and blends thereof.

The optional medicament-bearing layer is preferably applied to the parylene-containing layer from a solution using a simple spraying process. However, other application methods such as dipping, pipetting, and others may be used.

If the parylene-containing layer has regions with reduced thickness, the layer which bears an active substance is preferably provided in such a way that the active substance-bearing layer is not located where the regions of reduced layer thickness are present.

As stated above, a parylene-containing coating may preferably be applied using a plasma coating process. Gas processes as well as electrolytic plasma processes may be used. The plasma may be adjusted in a targeted manner for processing individual endoprostheses or geometric segments thereof, using suitable technical devices (shielding, gas flow, counterelectrode shape, etc.).

For modification of the coating, for example for varying the layer thickness over the surface of the endoprosthesis or the surface roughness, laser, electron, or ion radiation or electromagnetic fields, for example, may be used. The degradation regions may also be locally treated by bombardment with volatile solid bodies (dry ice, for example), thereby embrittling the coating at the treated sites in a localized surface region. A surface region of the layer may then be removed, using other processes such as laser, electron, or ion radiation, for example, resulting in a region with reduced layer thickness compared to the other regions. Modified regions may also be produced by bombardment with solid bodies (sand, ceramic, magnesium, salts, etc.), liquids (water jet, oils, acid, fats), or solid body/liquid mixtures. Degradation regions may also be produced by mechanical machining of the layer (needling, brush systems, for example) in drums or using vibratory grinding processes (trowalizing).

Appropriate lenses modified to the particular endoprosthesis geometry may be used in the production methods described above. For laser radiation, fiber optics may be used. In addition, highly dynamic handling techniques may be used, and regions of the coated endoprosthesis surface which are not to be machined may be shielded using masks.

In one particularly preferred production method for a parylene-containing coating having regions of reduced layer thickness, such regions are produced by etching in an oxygen plasma following application of the coating. Coatings with parylene types C and N generally result in macroscopically uniform coverage of the surface of the endoprosthesis. At the microscopic level, however, for both layer variants there are differences in thickness in the range of several 0.1 μm, but distributed over the surface of the endoprosthesis.

When an endoprosthesis surface covered with a parylene-containing coating of preferably 1 to 5 μm thickness is subjected to oxygen plasma treatment, the coating is attacked by the oxygen ions. This results in a locally selective reduction of the parylene-containing coating. This loss in the protective effect of the coating is inversely proportional to the layer thickness. The process parameters of the oxygen plasma (oxygen partial pressure, treatment time, chamber temperature, for example) are controlled in such a way that the weak points of the coating result at selected locations. In this manner degradation of the endoprosthesis material is accelerated in places, thus allowing the location of the degradation to be controlled. For etching of the coating, the plasma etching, reactive ion etching, and deep reactive ion etching processes may be used in an analogous manner.

Another possibility is to apply a resist to the coating. This resist is structured in such a way that removal of the coating, and therefore reduction in the layer thickness of the coating, occurs only at specific locations (predetermined breaking points) in a targeted manner. The resist is subsequently stripped using a wet chemical process.

Another possible production variant is a specialized shaping/machining of degradable endoprostheses, in which weak points are produced in the subsequently applied parylene layer. In this variant, predetermined breaking points are produced only during implantation of the endoprosthesis, not during the actual production thereof. These weak points (predetermined breaking points) are formed, for example, by holes or macropores in the webs of a stent, and are preferably introduced by laser cutting. This process step is applied in the course of the customary laser cutting process. The subsequent parylene coating initially results in a sealing effect, also for these predetermined breaking points. However, microcracks form during dilation of the stent, preferably in the vicinity of the zones containing the predetermined breaking points. These microcracks appear primarily in the areas characterized by the highest stress concentrations, around the predetermined breaking points. The corrosion attack then preferentially takes place at this location. The corrosion attack has the particular characteristic that it occurs in the zones around the predetermined breaking points at the same time and with equal intensity. The corrosion medium penetrates into the parylene layer subject to microcracks, corrodes the degradable material of the basic mesh located therebelow, and ultimately results in a cross-sectional weakening of the stent webs through corrosion attack which may be calculated within an accuracy of one week. Alternatively, predetermined breaking points are produced in the parylene layer at the parts of the stent which due to design reasons undergo great deformation at the surface as the result of crimping and dilation.

In a further exemplary embodiment of the invention, an adhesion-promoting layer is provided between the inert coating and the material of the basic mesh. Such an adhesion-promoting layer improves the adhesion between the coating and the material of the basic mesh. This type of adhesion-promoting layer may contain, for example, one or more compounds from the group of inorganic magnesium compounds (magnesium oxide, magnesium phosphate, etc.), or calcium phosphate.

For a structure of the endoprosthesis composed of support elements which preferably have a zigzag, meandering, or spiral design and perform the function of supporting the blood vessel or other hollow organs, and composed of connecting webs which join these support elements but have no supporting function themselves, in a further particularly preferred exemplary embodiment a plurality of regions having reduced layer thickness is provided only in the vicinity of the connecting webs. For example, each region of reduced layer thickness is provided only in the middle of a connecting web. Such an embodiment has a particularly simple design, and may also be implemented with low production costs. This type of endoprosthesis has the advantage that its collapse pressure drops very rapidly after a desired time period, such as four weeks to six months. Such an endoprosthesis is particularly desirable for clinical use.

The invention is explained in greater detail below with reference to exemplary embodiments illustrated by the figures. All of the described and/or illustrated features constitute the subject matter of the invention, regardless of their summary in the claims or back-reference.

DETAILED DESCRIPTION OF THE INVENTION

Figure 1:
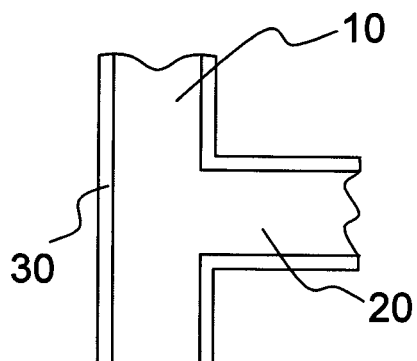
FIG. 1 shows a section of a first exemplary embodiment of an endoprosthesis according to the invention, in a cross-sectional view.

FIG. 1 shows a section of a basic mesh of an endoprosthesis according to the invention, designed as a stent. The basic mesh has webs that are folded in a zigzag or meandering shape, extending essentially in the circumferential direction, or helical webs, as support elements 10, and has webs which extend essentially in the longitudinal direction of the stent as connecting webs 20. The stent has an overall design of a tubular or hollow cylindrical endoprosthesis, open at its ends and extending in the direction of the connecting webs 20. In FIG. 1 only one section of the basic mesh is illustrated, in which the end of a connecting web 20 abuts against a support element 10.

The basic mesh of the stent is composed, at least predominantly, of one or more of the above-referenced materials which are predominantly biodegradable, preferably made of magnesium or a magnesium alloy, particularly preferably WE43. The basic mesh has over its entire surface a parylene-containing coating 30, with an essentially constant layer thickness, which completely covers the basic mesh. The layer thickness is between approximately 0.1 µm and approximately 10 µm, preferably between approximately 0.4 µm and approximately 7 µm, particularly preferably between approximately 1 µm and approximately 5 µm. Examples of suitable materials for the coating 30 are parylene C or parylene N, the coating 30 preferably being composed completely, or at least 90% by weight, of parylene C or parylene N.

Figure 2:
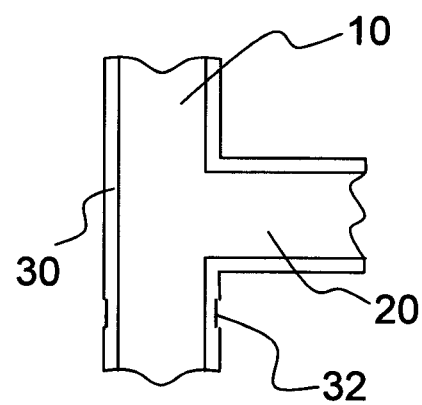
FIG. 2 shows a section of a second exemplary embodiment of an endoprosthesis according to the invention, in a cross-sectional view.

In the second exemplary embodiment of a stent according to the invention illustrated in FIG. 2, provided in the vicinity of the support element 10 is an annular region 32 which encloses the support element 10 and in which the coating 30 has a reduced layer thickness. By use of such a region 32 it is possible to precisely control the location at which the degradation of the stent according to the invention proceeds at a higher speed.

Figure 3:
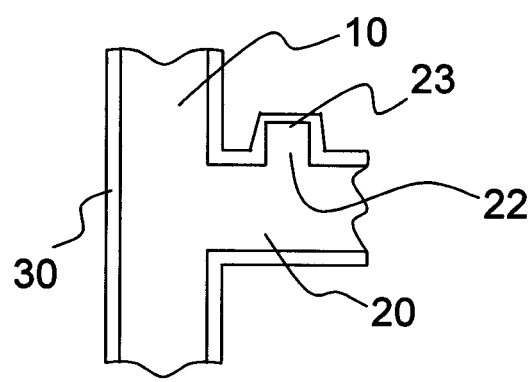
FIG. 3 shows a section of a third exemplary embodiment of an endoprosthesis according to the invention, in a cross-sectional view.

The exemplary embodiment illustrated in FIG. 3 has a region 22, in the form of a finger-shaped projection which is made of the same material as the stent, on a plurality of connecting webs 20. The finger-shaped projection 22 has an essentially cylindrical shape, which in a further exemplary embodiment not illustrated may taper, i.e., have a reduction in its diameter, in the direction facing away from the basic mesh. The coating 30 is provided with a reduced layer thickness at the end 23 projecting away from the connecting web 20. The same as in the second exemplary embodiment, this causes more rapid degradation of the material of the endoprosthesis in the region of the end 23 of the projection 22.

Figure 4:
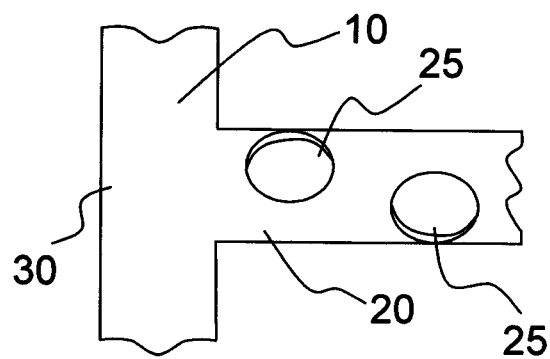
FIG. 4 shows a section of a fourth exemplary embodiment of an endoprosthesis according to the invention, in a side view.

In the fourth exemplary embodiment illustrated in FIG. 4, circular regions 25 are preferably provided on the connecting webs 20 in which the coating 30 has a reduced layer thickness. After insertion into the body the stent degrades more rapidly at these locations as well.

The illustrated exemplary embodiments for the provision of the regions with a reduced layer thickness may be varied at will, depending on the desired degradation characteristics. Thus, the finger-shaped projections 22 may also be provided on the support elements 10 or at other locations on the connecting webs 20. In addition, the finger-shaped projections 22 may be provided at multiple locations on the support elements, or only on specific support elements 10 or connecting webs 20. The same applies for the annular regions 32 or the circular regions 25. The various types of shapes of the regions having reduced layer thickness may be varied at will and/or combined with one another as desired on an endoprosthesis.

The endoprostheses may be manufactured by first producing the endoprosthesis from the biodegradable material, using the known production methods. The finger-shaped projections 22 or other degradation elements may optionally be provided on the basic mesh at the desired locations. The coating 30 is then applied using known coating processes (for parylene, for example, by using a plasma coating process or gas phase deposition process), whereby at the locations at which degradation regions having a reduced layer thickness are to be provided, during the coating a cover is provided in places so that the coating is not applied in parts of these regions during the coating process. Stencils, for example, may be used for this purpose. The cover is then removed. Alternatively, the coating may first be applied uniformly or homogeneously to the entire surface of the endoprosthesis and then partially removed in some regions, thereby structuring the surface of the stent.

Figure 5A:
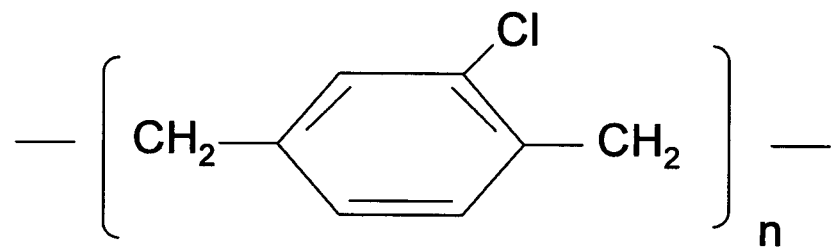
FIG. 5 shows the structural formulas of parylene C (FIG. 5*a*) and parylene N (FIG. 5*b*)
Figure 5B:
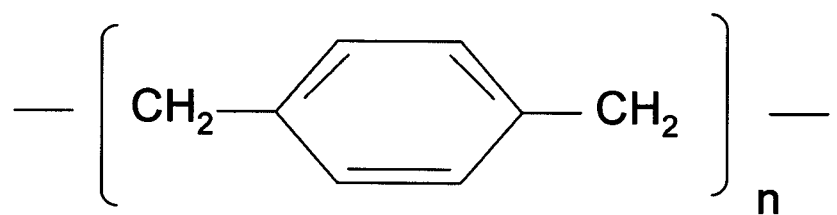

The structural formulas of parylene C and parylene N, each of which represents a preferred material for the coating 30, are shown in FIG. 5a and FIG. 5b, respectively.

Figure 6:
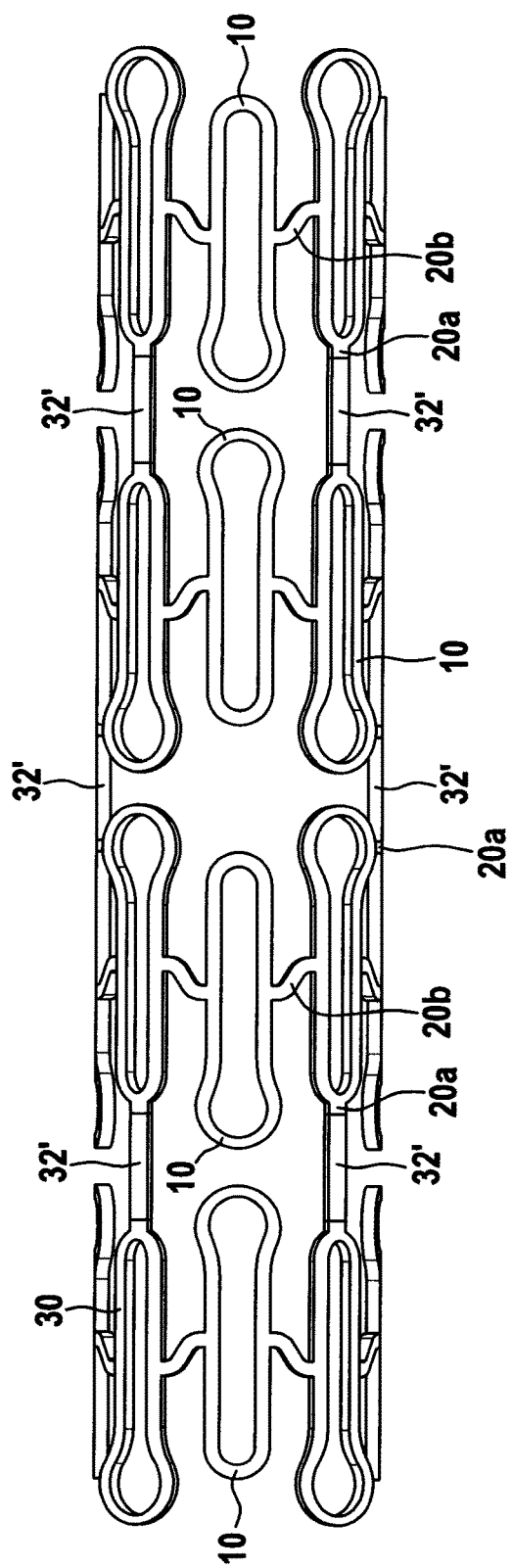
FIG. 6 shows a section of a fifth exemplary embodiment of an endoprosthesis according to the invention, in a side view.

FIG. 6 shows once again a longer section of an endoprosthesis according to the invention in the form of a stent, which on the connecting webs 20a of the support elements 10 extending in the longitudinal direction has annular and circumferential regions 32' of reduced layer thickness of the coating 30 which extend over almost the entire length of the connecting webs 20a. The connecting webs 20b of the support elements 10 which extend not in the longitudinal direction, but instead are curved essentially in the radial direction, have no regions of reduced layer thickness.

The regions of reduced layer thickness have a layer thickness of 0% to 70%, preferably 5% to 50%, of the layer thickness in the other regions.

Figure 7:
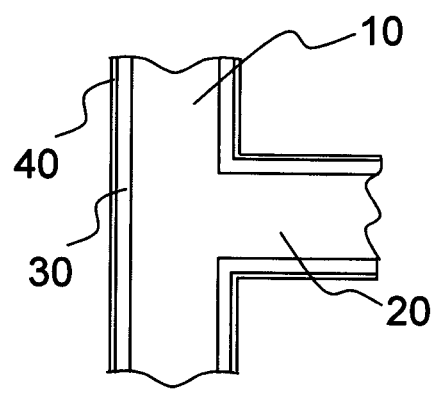
FIG. 7 shows a section of a sixth exemplary embodiment of an endoprosthesis according to the invention, in a cross-sectional view, together with an additional layer containing an active substance.

FIG. 7 illustrates a further exemplary embodiment of an endoprosthesis according to the invention, whose structure corresponds to the first exemplary embodiment illustrated in FIG. 1. The endoprosthesis shown has an additional layer 40 which contains a carrier, preferably made of a degradable polymer, and at least one of the pharmaceutically active substances referenced above, which are provided on the surface of the parylene-containing coating 30.

Figure 8:
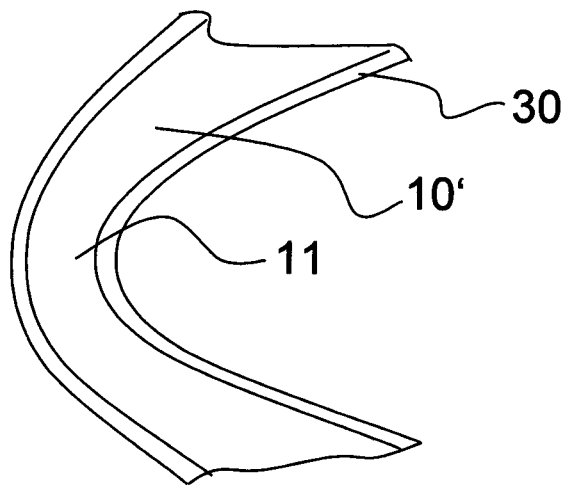
FIGS. 8 and 9 show a cross section of part of the support structure in a seventh exemplary embodiment of an endoprosthesis according to the invention.

FIG. 8 illustrates a section of a support element 10' of a seventh exemplary embodiment of the endoprosthesis according to the invention, in the form of a stent. The section shows a bend or curvature 11 in a support element 10', the surface of the support element 10' forming a peak when viewed in the cross section. The support element 10' made of the biodegradable material has a slightly smaller diameter in the region of the curvature 11 than in the other regions. A uniform parylene-containing coating 30 is provided on the surface of the support element which completely covers the surface.

Figure 9:
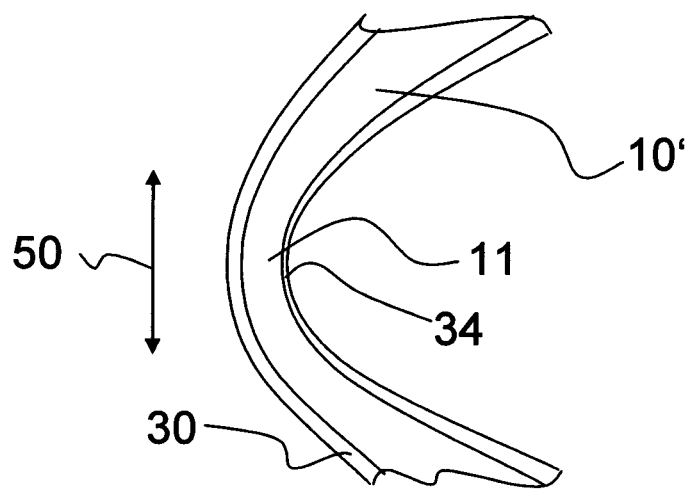

As shown in FIG. 9, for the dilation of the endoprosthesis, designed as a stent, in the lesion in the direction of dilation 50, as the result of the thinner design of the biodegradable material the support element 10' is bent back more strongly in the region of the curvature 11 than in the other regions of the support element 10'. Due to the stretching in direction 50 (radial direction of the stent) the support element 10' attempts to straighten the curvature back. As a result of the bending back of the curvature 11 a region 34 of the coating 30 is stretched more intensely on the inner side, i.e., in the concave region, of the curvature 11, so that after the dilation is completed the coating is less thick in region 34 than in the other regions. As a result, the degradation attack takes place first in region 34 after implantation of the endoprosthesis according to the invention.

In a further exemplary embodiment, as an addition or alternative to the exemplary embodiment illustrated in FIGS. 8 and 9 having a smaller diameter of the support element, a notch may be provided in the region of the inner side of the curvature 11. In a manner analogous to the design with a smaller diameter, the notch is used so that the support element is bent back to the maximum in this region. Here as well, this causes the parylene-containing coating situated above the support element to undergo the most stretching in this region, so that more intense degradation occurs in this region.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMERALS 10, 10' Support element
11 Curvature of the support element
20, 20a, 20b Connecting web
22 Finger-shaped projection
23 End of the finger-shaped projection 22 protruding away
25 Circular region with reduced thickness of the coating 30
30 Coating
32, 32' Annular region with reduced thickness of the coating 30
34 Region with reduced thickness of the coating 30
40 Layer containing an active substance
50 Direction of dilation

What is claimed is:

1. An endoprosthesis having a basic mesh comprised of a biodegradable material consisting essentially of one or more of Mg, or Mg alloy, a coating completely covering the basic mesh, and an adhesion-promoting layer between the basic mesh and the coating, characterized in that the coating contains parylene, the adhesion-promoting layer consists of one or more of inorganic magnesium compounds, magnesium oxide, magnesium phosphate, or calcium phosphate, the coating has regions in which a thickness of the coating is reduced compared to a thickness of the coating in other regions, and the thickness of the coating in all regions is between 0.1 μm and 10 μm, and wherein the thickness of the coating on the reduced thickness region is greater than 0% and less than or equal to 70% of the thickness of the coating in the other regions.

2. The endoprosthesis according to claim 1, wherein the adhesion-promoting layer is selected from the group consisting of one or more of the magnesium phosphate, or the calcium phosphate.

3. The endoprosthesis according to claim 1, characterized in that the biodegradable material consists essentially of WE43.

4. The endoprosthesis according to claim 1, characterized in that the coating additionally contains one or more polymers selected from the group comprising polyesters, polylactides, and polypeptides.

5. The endoprosthesis according to claim 1, characterized in that a layer containing at least one pharmaceutically active substance is applied to at least a portion of the coating.

6. The endoprosthesis according to claim 5, characterized in that the layer with the pharmaceutically active substance contains a degradable polymer as carrier.

7. The endoprosthesis according to claim 1 wherein the endoprosthesis is an intraluminal endoprosthesis, and wherein the coating comprises at least 60 wt % parylene.

8. The endoprosthesis according to claim 1 wherein the endoprosthesis is a stent, and wherein the coating comprises at least 90 wt % parylene C.

9. The endoprosthesis according to claim 1 wherein the coating comprises at least 90 wt % parylene N.

10. The endoprosthesis according to claim 1 wherein the coating thickness is between 0.4 μm and 7 μm.

11. The endoprosthesis according to claim 1 wherein the coating thickness is between 1 μm and 5 μm.

12. The endoprosthesis according to claim 1 wherein the endoprosthesis maintains integrity for a period of four weeks to six months.

13. The endoprosthesis according to claim 1 wherein the basic mesh comprises support elements and connecting webs, and wherein the coating region having reduced thickness is on the connecting web.

14. The endoprosthesis according to claim 1 wherein the thickness of the coating region having reduced thickness is 5% to 50%, of the thickness of the coating in the other regions.

15. The endoprosthesis according to claim 1 wherein the basic mesh comprises support elements and connecting webs, and wherein the connecting web has a projection extending away from the connecting web.

16. The endoprosthesis according to claim 15 wherein the coating region of reduced thickness is on the projection.

17. An endoprosthesis having a basic mesh comprised of a biodegradable material consisting essentially of one or more of Mg, or Mg alloy, a coating completely covering the basic mesh, an adhesion-promoting layer between the basic mesh and the coating, and a layer containing at least one pharmaceutically active substance applied to at least a portion of the coating, wherein the coating contains parylene, the adhesion-promoting layer is selected from the group consisting of one or more of inorganic magnesium compounds, magnesium oxide, magnesium phosphate, or calcium phosphate, the coating has regions in which a thickness of the coating is reduced compared to a thickness of the coating in other regions, and the thickness of the coating in all regions is between 0.1 μm and 10 μm, and wherein the thickness of the coating on the coating region having reduced thickness is greater than 0% and less than or equal to 70% of the thickness of the coating in the other regions, and wherein the layer containing the at least one pharmaceutically active substance is not located on the coating region having reduced thickness.

18. The endoprosthesis according to claim 17 wherein the thickness of the coating region having reduced thickness is 5% to 50% 70% of the thickness of the coating in the other regions.

19. An endoprosthesis having a basic mesh comprised of a biodegradable material consisting essentially of one or more of Mg, or Mg alloy, the basic mesh comprising support elements and connecting webs, the support elements comprising webs formed in a zigzag or meandering shape or belical webs formed in a zigzag or meandering shape, the support elements extending in the circumferential direction of the endoprosthesis, the connecting webs comprising webs extending in the longitudinal direction of the endoprosthesis and webs extending in the radial direction of the endoprosthesis, and a coating provided above the biodegradable material, characterized in that the coating contains parylene, and the basic mesh is completely covered by the coating, whereby the thickness of the coating in all regions is between 0.1 μm and 10 μm, wherein the coating has a reduced thickness on the longitudinally extending connecting webs, and wherein the reduced thickness region of the coating is greater than 0% and less than or equal to 70% of the thickness of the coating on the support elements.

* * * * *